(12) United States Patent
Hanna et al.

(10) Patent No.: US 10,160,946 B2
(45) Date of Patent: Dec. 25, 2018

(54) PLURIPOTENT TISSUE HARVESTER AND METHODS OF MANUFACTURE THEREOF

(71) Applicant: UNIVERSITY OF FLORIDA RESEARCH FOUNDATION, INC., Gainesville, FL (US)

(72) Inventors: Mina-Elraheb Saad Hanna, Stanford, CA (US); Juan Claudio Nino, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 146 days.

(21) Appl. No.: 14/917,035

(22) PCT Filed: Sep. 12, 2014

(86) PCT No.: PCT/US2014/055342
§ 371 (c)(1),
(2) Date: Mar. 7, 2016

(87) PCT Pub. No.: WO2015/038865
PCT Pub. Date: Mar. 19, 2015

(65) Prior Publication Data
US 2016/0215250 A1    Jul. 28, 2016

Related U.S. Application Data

(60) Provisional application No. 61/877,537, filed on Sep. 13, 2013.

(51) Int. Cl.
*C12N 5/00* (2006.01)
*C12M 3/00* (2006.01)
(Continued)

(52) U.S. Cl.
CPC ............ *C12M 33/00* (2013.01); *C12M 21/08* (2013.01); *C12M 23/02* (2013.01); *C12M 25/00* (2013.01); *C12M 35/04* (2013.01)

(58) Field of Classification Search
CPC ...... C12M 33/00; C12M 21/08; C12M 23/02; C12M 25/00; C12M 35/04; C12N 2535/00; C12N 2535/10
See application file for complete search history.

(56) References Cited

U.S. PATENT DOCUMENTS 7,772,001 B2    8/2010    Benvenisty
8,941,059 B2    1/2015    Sato
(Continued)

FOREIGN PATENT DOCUMENTS

WO    WO9711646 A1    4/1997

OTHER PUBLICATIONS

Fachin, F., 3D MEMS via (post-) buckling of micromachined structures and integration of bulk nanoporous elements in microfluidic devices. Massachusetts Institute of Technology [online], Jun. 2011 [retrieved on Aug. 18, 2017]. Retrieved from the Internet: <URL: http://hdl.handle.net/1721.1/85759>.*

(Continued)

*Primary Examiner* — Kara D Johnson
(74) *Attorney, Agent, or Firm* — Timothy H. Van Dyke; Beusse, Wolter, Sanks & Maire PLLC

(57) ABSTRACT

Disclosed herein is a tissue harvester comprising a substrate having an airfoil shape; and a textured surface disposed upon the substrate, where the textured surface comprises a spatial array of nanometer or micrometer sized pillars of varying cross-sections. Disclosed herein too is method comprising disposing upon a substrate a textured surface; where the substrate has an airfoil shape and where the textured surface where the textured surface comprises nanometer or micrometer sized pillars; contacting the tissue harvester with biological cells whose proliferation under different conditions is desired; and disposing the tissue harvester in a flow (Continued)

field such that cells disposed on the tissue harvester at different locations may experience different flow fields.

14 Claims, 4 Drawing Sheets

(51) Int. Cl.
*C12M 1/26* (2006.01)
*C12M 1/00* (2006.01)
*C12M 1/12* (2006.01)
*C12M 1/42* (2006.01)

(56) References Cited

U.S. PATENT DOCUMENTS

| | | |
|---|---|---|
| 9,149,564 B2 | 10/2015 | Jin |
| 2004/0171153 A1 | 9/2004 | Andrews |
| 2006/0057657 A1 | 3/2006 | Baetscher |
| 2008/0057571 A1 | 3/2008 | Loboa |
| 2010/0197007 A1 | 8/2010 | Cailleret |
| 2012/0035618 A1 | 2/2012 | Sabir |
| 2013/0143313 A1 | 6/2013 | Niazi |

OTHER PUBLICATIONS

Lobo et al., An evaluation of cell proliferation and adhesion on vertically-aligned multi-walled carbon nanotube films. Carbon, vol. 48, No. 1 (Jan. 2010) pp. 245-254.*
Cohen, D. M. et al. "Mechanical control of stem cell differentiation." In: Sangeeta Bhatia JP, editor. StemBook. 1st ed. Cambridge, MA: 2008. p. 1.
Dalby MJ, et al. "The control of human mesenchymal cell differentiation using nanoscale symmetry and disorder," Nature materials. 2007; 6:997.
Dennis, J. E., K. Esterly, et al. "Clinical-scale expansion of a mixed population of bone marrow-derived stem and progenitor cells for potential use in bone tissue regeneration." Stem Cells 25(10): 2575-2582. 2007.
Engelmayr, G. C., et al. "A novel flex-stretch-flow bioreactor for the study of engineered heart valve tissue mechanobiology." Annals of Biomedical Engineering 36(5): 700-712. 2008.
Engler AJ, et al. "Matrix elasticity directs stem cell lineage specification." Cell. 2006 8/25:126(4):677-89.
Even-Ram S, et al. "Matrix control of stem cell fate." Cekk. 2006; 126:645.
Illi B, et al. "Epigenetic histone modification and cardiovascular lineage programming in mouse embryonic stem cells exposed to laminar shear stress." Journal of the American Heart Association. (2005) 501-508.
International Preliminary Report on Patentability for International Application No. PCT/US2014/055342; International Filing Date Sep. 12, 2014; Dated Mar. 15, 2016 (7 pages).
International Search Report for International Application No. PCT/US2014/055342; International Filing Date Sep. 12, 2014; Dated Dec. 24, 2014 (5 pages).
King, J. A., et al. "Bioreactor Development for Stem Cell Expansion and Controlled Differentiation" Current Opinion in Chemical Biology 11(4): 394-398. 2007.
Oh, S. K. W., et al. "High density cultures of embryonic stem cells." Biotechnology and Bioengineering 91(5): 523-533. 2005.
Stolberg S., et al. "Can shear stress direct stem cell fate?" Biotechnol Prog. 2009; 25(1):10-9.
Takahashi K, et al. "Induction of pluripotent stem cells from mouse embryonic and adult fibroblast cultures by defined factors." Cell. 2006 8/25;126(4):663-76.
Written Opinion for International Application No. PCT/US2014/055342; International Filing Sep. 12, 2014; Dated Dec. 24, 2014 (6 pages).
Yamamoto K, et al. "Fluid shear stress induces differentiation of Flk-1-positive embryonic stem cells into vascular endothelial cells in vitro." American Journal of Physiology. 2004 (288):H1915.
Yamamoto, K. et al. "Proliferation, differentiation, and tube formation by endothelial progenitor cells in response to shear stress." Journal of Applied Physiology. 2003 (95):2088.
Zhang, H. et al. "Gene expression of single human mesenchymal stem cell in response to fluid shear." Journal of Tissue Engineering. (2012) 3(1) (8 Pages).
Zhang, P. et al. "Endothelial differentiation of amniotic fluid-derived stem cells: Synergism of biochemical and shear force stimuli." Stem Cells and Development. 2009;18(9)1299.

* cited by examiner

PLURIPOTENT TISSUE HARVESTER AND METHODS OF MANUFACTURE THEREOF

CROSS-REFERENCE TO RELATED APPLICATIONS

This application claims priority to International Application No. PCT/US14/055342 filed on 12 Sep. 2014, which claims the benefit of U.S. Provisional Application No. 61/877,537, filed on 13 Sep. 2013, which is incorporated herein by reference in its entirety.

BACKGROUND

Stem cells are biological cells found in all multicellular organisms that can divide (through mitosis) and differentiate into diverse specialized cell types and can self-renew to produce more stem cells. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells (ectoderm, endoderm and mesoderm—these are called pluripotent cells), but also maintain the normal turnover of regenerative organs, such as blood, skin, or intestinal tissues.

There are three accessible sources of autologous adult stem cells in humans:

a) bone marrow, which requires extraction by harvesting, that is, drilling into bone (typically the femur or iliac crest), b) adipose tissue (lipid cells), which uses extraction by liposuction, and c) blood, which uses extraction through pheresis, wherein blood is drawn from the donor (similar to a blood donation), passed through a machine that extracts the stem cells and returns other portions of the blood to the donor.

Stem cells can also be taken from umbilical cord blood just after birth. Of all stem cell types, autologous harvesting involves the least risk. By definition, autologous cells are obtained from one's own body, just as one may bank his or her own blood for elective surgical procedures.

Highly plastic adult stem cells are routinely used in medical therapies, for example in bone marrow transplantation. Stem cells can now be artificially grown and transformed (differentiated) into specialized cell types with characteristics consistent with cells of various tissues such as muscles or nerves through cell culture. Embryonic cell lines and autologous embryonic stem cells generated through therapeutic cloning have also been proposed as promising candidates for future therapies.

It is therefore desirable to have a tissue harvester that can generate cells under a variety of different conditions for use in various medical therapies.

SUMMARY

Disclosed herein is a tissue harvester comprising a substrate having an airfoil shape; and a textured surface disposed upon the substrate, where the textured surface comprises nanometer or micrometer sized pillars and related architectures.

Disclosed herein too is method comprising disposing upon a substrate a textured surface; where the substrate has an airfoil shape and where the textured surface where the textured surface comprises nanometer or micrometer sized pillars of varying cross-section and spacing; contacting the tissue harvester with biological cells whose proliferation under different conditions is desired; and disposing the tissue harvester in a flow field such that cells disposed on the tissue harvester at different locations may experience different flow fields.

DETAILED DESCRIPTION

Disclosed herein is a pluripotent tissue harvester (hereinafter tissue harvester) that has at least a portion having an airfoil shape and comprises a substrate upon which is disposed a textured surface. The textured surface comprises a spatial array of pillars, where both the spatial array and cross-section of the pillars can vary. For example, nanometer sized (less than 100 nanometer sized pillars) and/or micrometer sized (100 nanometers to 10 micrometers) pillars that can have the same stiffness or a different stiffness from that of the substrate. The tissue harvester allows for a systematic variation of the Reynolds number, thereby exposing pluripotent stemless cells to both laminar and turbulent flow. This shape of the harvester facilitates a precise variance in shear force in one experimental run. In addition, the harvester allows for a large scale generation of a cell viable cell source that can be from autografts (same patient), xenografts (from other species), or allografts (from other patients). The ability of the harvester to change surface conditions by virtue of its airfoil shaped profile facilitates directed differentiation of cells as a function of cell location on the tissue harvester. Further, it simulates the function of the extracellular matrix by providing a path for nutrients to be delivered to the cells, and for waste to be taken away, thus eliminating the chief source of necrosis in current three-dimensional scaffolds.

The profile or shape of the airfoil can be used to create shear and/or turbulent flow conditions that cell cultures on the harvester can be subjected to. The shape of the airfoil when combined with different surface nano- and microstructures can establish specific regimes and shear stress conditions under pulsating flow that will lead to differentiation in the flow field that the cell cultures are subjected to. The shape or cross section profile of the airfoil leads to different flow conditions (pressure, speed, laminar versus turbulent flow conditions, and the like) depending on where in the airfoil the cells are located. The surface texture of the airfoil leads to different attachment conditions for the cells that can further modify the shear stress conditions that the cells experience.

The airfoil shaped tissue harvester can be subjected to a variety of different flow fields. The cells disposed on the airfoil shaped tissue harvester can be subjected to laminar flow and/or turbulent flow depending upon their location, on the harvester. The cells in a single location can also be subjected to pulsating flow caused by varying flow rate (speed) and frequency of flow pulsation. This will lead to different levels of shear stress and thus present a different environment for the cells, even if the same airfoil profile and the same surface texture are used.

Figure 1:
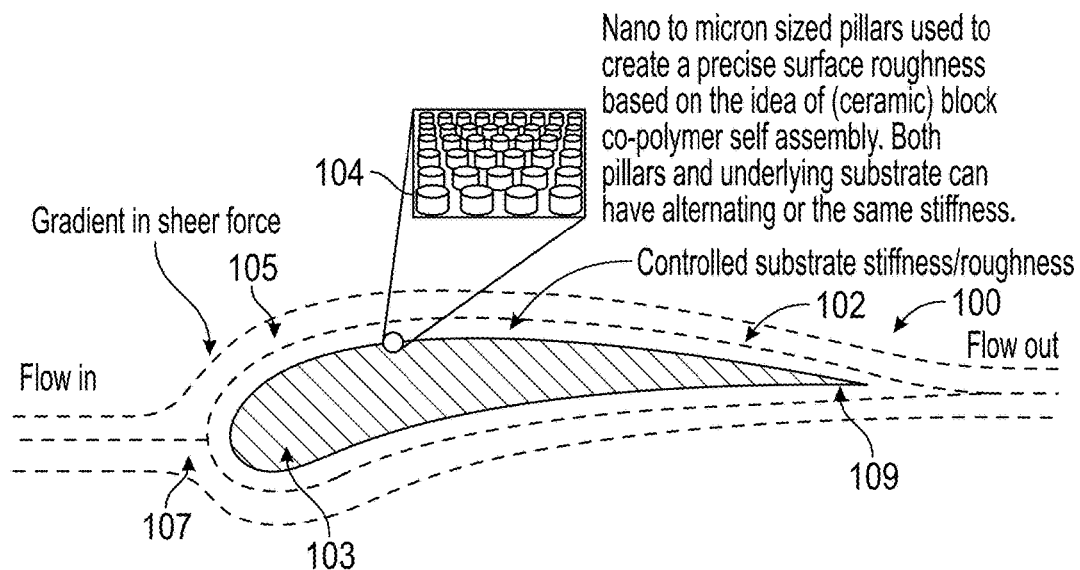
FIG. 1 is a depiction of an exemplary tissue harvester having an airfoil shape.

The FIG. 1 depicts a side view of a tissue harvester 100 that comprises a substrate 102 upon which is disposed a textured surface 104. The textured surface 104 and the substrate 102 may be monolithic (i.e., they are a single indivisible piece) or alternatively the textured surface 104 may be disposed on the substrate 102 in the form of a coating. The textured surface 104 lies on the outer surface of the substrate 102.

The substrate 102 has an air-foil like shape with one surface i.e., a first surface 103 being concave and the opposing surface—a second surface 105 being convex. The surfaces 103 and 105 contact each other at opposing ends 107 and 109. The substrate may be derived from an organic polymer, a ceramic, a metal, or a composite. As an example, the airfoil shaped substrate has a length "l" that is at least 5 times greater than the width "w", preferably at least 10 times greater than the width, and more preferably at least 15 times greater than the width. However, the overall dimensions of the airfoil and in particular, its profile can be varied accordingly to obtain the desired shear stress and laminar or turbulent flow conditions, and the size of the tissue to be harvested.

Figure 2:
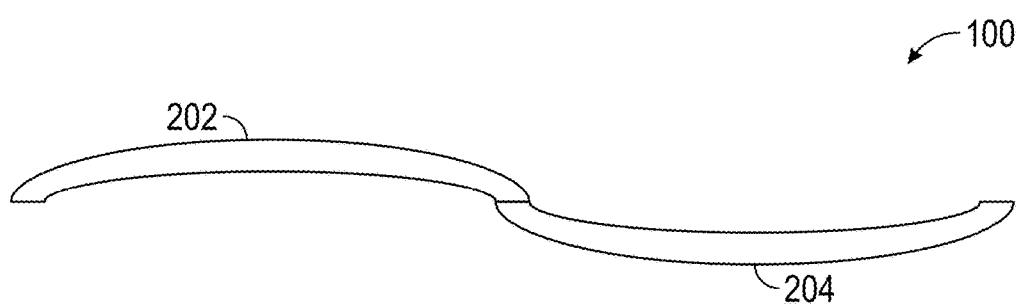
FIG. 2 is a depiction of an exemplary tissue harvester that comprises a plurality of airfoils.

As noted above, the substrate may comprise one or more airfoils as shown in the FIG. 2. In the FIG. 2, the airfoil 100 comprises a first airfoil 202 in contact with a second airfoil 204. The second airfoil 204 is disposed so that it faces the opposite direction from the first airfoil 202. In this manner, a plurality of airfoils may be in communication with one another to form the pluripotent tissue harvester. Alternatively, the airfoil may be part of a larger substrate, where the larger substrate as a whole is not an airfoil.

While biocompatibility is important for the material selection for the airfoil manufacturing, organic polymers used for the substrate or for the textured surface may be selected from a wide variety of thermoplastic polymers, blend of thermoplastic polymers, thermosetting polymers, or blends of thermoplastic polymers with thermosetting polymers. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, an ionomer, or the like, or a combination comprising at last one of the foregoing organic polymers.

Examples of the organic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination comprising at least one of the foregoing organic polymers.

Examples of thermosetting polymers suitable for use in the polymeric composition include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleicanhydride/acrylonitrile-butadiene-styrene, polyether etherketone/polyethersulfone, polyether etherketone/polyetherimide polyethylene/nylon, polyethylene/polyacetal, or the like.

When the polymers are used in the textured surface 104, it is desirable to create reactive groups on the surface. This may be accomplished by treating the surface with radiation. Examples of such radiation are ionizing radiation (where the surface is bombarded with ions), xrays, electron beams, neutron beams, and the like.

Examples of ceramics are metal oxides such as alumina, silica, titania, zirconia, ceria, quartz, or the like, or a combination comprising at least one of the foregoing metal oxides. Examples of suitable metals are copper, iron, aluminum, tin, zinc, gold, silver, tantalum, lead, manganese, nickel, chromium, molybdenum, titanium, vanadium, niobium, or the like, or a combination comprising at least one of the foregoing metals, or alloys thereof.

In an exemplary embodiment, the substrate and the textured surface are manufactured from an identical material.

While the substrate may not necessarily be biocompatible, it is desirable for the textured surface to be biocompatible. In one embodiment, the textured surface and/or the substrate can be manufactured from a block copolymer. Exemplary block copolymers that are contemplated for use in the textured surface include diblock or triblock copolymers such as poly(styrene-b-vinyl pyridine), poly(styrene-b-butadiene), poly(styrene-b-isoprene), poly(styrene-b-methyl methacrylate), poly(styrene-b-alkenyl aromatics), poly(isoprene-b-ethylene oxide), poly(styrene-b-(ethylene-propylene)), poly(ethylene oxide-b-caprolactone), poly(butadiene-b-ethylene oxide), poly(styrene-b-t-butyl (meth)acrylate), poly(methyl methacrylate-b-t-butyl methacrylate), poly(ethylene oxide-b-propylene oxide), poly(styrene-b-tetrahydrofuran), poly(styrene-b-isoprene-b-ethylene oxide), poly(styrene-b-dimethylsiloxane), poly(methyl methacrylate-b-dimethylsiloxane), or a combination comprising at least one of the foregoing block copolymers. The block copolymers are disposed upon the substrate so that they form cylindrical domains or lamellar domains that are perpendicularly disposed to the surfaces 103 and 105 of the substrate. In an exemplary embodiment, the textured surface is biocompatible and comprises a fluorocarbon, a polysiloxane, or a combination thereof.

In an embodiment, the cylindrical domains of the block copolymer are retained while the surrounding portion of the block copolymer are removed by etching to form a textured surface. In another embodiment, a block copolymer may be used as a template to pattern the surfaces 103 and 105 to form the textured surfaces. The block copolymer may be used as a negative template or as a positive template to form cylindrical domains (pillars) on the surface as shown in the FIG. 1. It is to be noted that while the domains are described as being cylindrical, they may also be square, rectangular, triangular, or polygonal in shape. Combinations of shapes may also be used. Different surfaces of the airfoil may employ different textures.

The texturing may be projected outwards from the surface (i.e., embossed on the surface) or may be projected into the surface. The texturing may be accomplished by scratching the surface with a tool or implement. The surface roughness of the textured surface may vary from 2 to 50.

In one embodiment, the cylindrical domains may have a diameter in the nanometer range of less than 100 nanometers or less, specifically 75 nanometers or less, and more specifically 50 nanometers or less. In another embodiment, the cylindrical domains have diameters in the micrometer size range. The diameters can be greater than 100 nanometers, specifically greater than 1 micrometer, and more specifically greater than 5 micrometers, and more specifically greater than or equal to 10 micrometers. The aspect ratio of the cylindrical domains can be varied along the length of the surface if desired. The aspect ratio can be varied from 1:1 to 10:1, specifically 2:1 to 5:1. Furthermore, besides the aspect ratio, the spatial distribution and pattern or lattice of the domains is of utmost importance in promoting aligned cell proliferation and growth of tissue.

FIG. 1 details pillars (cylindrical domains). However, other geometrical objects may be used instead of pillars. For examples, the textured surface can have other 3-dimensional objects disposed on the surface or projected into the surface. Examples of such 3-dimensional objects are pyramids (triangular, rectangular, square, and polygonal), cones, conical sections, cubes, cuboids, prisms, spheres, hemispheres, or the like, or a combination comprising at least one of the foregoing geometrical shapes. The 3-dimensional objects can have cross sectional areas that are square, circular, ellipsoidal, triangular, or polygonal.

It is preferable for the textured surface to be reactive so that cells can adhere to the surface and proliferate. The surface chosen for the growth of a particular cell culture can be varied depending on the type of cell culture, the amount of proliferation desired, and the like.

In one embodiment, in one method of forming the tissue harvester 100, the substrate 102 is first machined or molded. After the substrate 102 is manufactured or after the respective surfaces 103 and 105 of the substrate are manufactured in the desired shapes, a textured surface 104 is prepared. The textured surface 104 may be prepared separately and bonded to the substrate surfaces 103 and 105 or alternatively may be prepared directly on the respective surfaces 103 and 105 by using a template and etching the surfaces as described above. In another embodiment, the tissue harvester can be manufactured using 3D printing (also termed additive manufacturing). Additive manufacturing or 3D printing is a process of making a three-dimensional solid object of virtually any shape from a digital model. 3D printing is achieved using an additive process, where successive layers of material are laid down in different shapes. 3D printing is considered distinct from traditional machining techniques, which mostly rely on the removal of material by methods such as cutting or drilling (subtractive processes). A materials printer usually performs 3D printing processes using digital technology. The surfaces 103 and 105 may then be subjected to plasma treatment, or radiation using ions, electrons, X-rays, and the like in order to produce a reactive surface.

In another embodiment, the tissue harvester can be manufactured by injection molding polystyrene petri dishes with the requisite textured surfaces. The molded surface is then treated in a plasma field and then subjected to treatment with chemicals such as collagen, poly-L-Lysine, poly-D-Lysine, gelatin, vironectin, osteopontin, collagen, fibronectin, superfibronectin, Hydromatrix™ Peptide Cell Culture Scaffold, Maxgel™, E-Cadhein/Fc Chimera, and the like. These chemicals facilitate bonding of the cells to the textured surface.

The device is then disposed in a flow field, where cells along with a fluid may contact the tissue harvester. The tissue harvester can be manufactured in any size. In one embodiment, the tissue harvester can be of a size that fits in a petri dish having a diameter of 10 centimeters. In another embodiment, it could be large enough to fit in a 100,000 gallon water tank or in an autoclave. The tissue harvester can have a surface area of 10 square millimeters to 100,000 square meters, preferably 100 square millimeters to 10,000 square meters.

In one embodiment, in one method of using the tissue harvester, cells of a particular type may be disposed in the harvester in a flow field. The airfoil shape of the tissue harvester permits proliferation of the cells at various fluid flow regimes in the tissue harvester. The fluid flow regimes include laminar flow as well as turbulent flow. Depending upon the velocity of the flow field, some areas of the tissue harvester may even experience a local vacuum (negative pressure with respect to the atmosphere). With reference now to the FIG. 1, as the fluid flows over the airfoil shaped tissue harvester, there is a gradient in shear force at the surface. The fluid layers near the surface are laminar, while as the distance from the surfaces is increased, the fluid flow becomes turbulent. In an embodiment, the flow field in the tissue harvester is a pulsating field. The tissue harvester and the cells disposed thereon therefore experience a flow field gradient that ranges from laminar to turbulent.

The tissue harvester described herein has a number of advantages—notably the fluid flow can be varied from laminar to turbulent. This shape of the harvester facilitates a precise variance in shear force in one experimental run. The ability of the harvester to change the surface conditions by virtue of its airfoil shaped profile shaped apparatus, induces differentiation, and simulates the function of the extracellular matrix, providing a path for nutrients to be delivered to the cells, and for waste to be taken away, thus eliminating the chief source of necrosis in current three-dimensional scaffolds.

The manufacturing and shape of the tissue harvester is now described in detail with respect to the following non-limiting example.

Example

Deformation of a standard cell culture dish (FisherSci 12-565-90) to induce an airfoil shape was done by inverting a petri-dish, heating the substrate (MicroTouch MT 770) for 2-3 seconds and placing a steel sphere on it (McMaster-Carr 96455K56). By using a hot needle, further modification of the petri-dish base and cap allowed for barbed couplings (McMaster-Carr 51525K213, 7370A38).

Figure 3A:
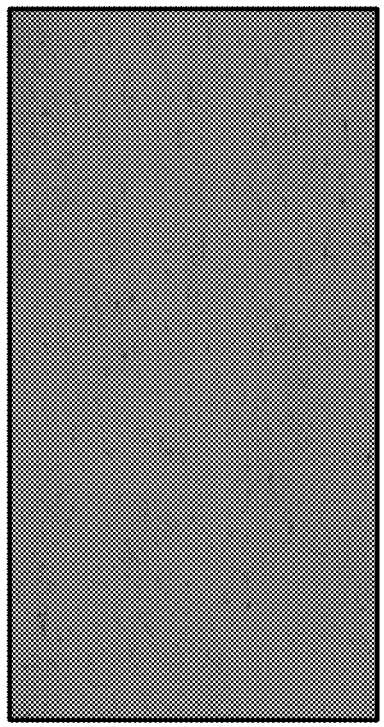
FIGS. 3A-3C are photomicrographs showing primary rat cardiac progenitor cells on three separate cell culture dishes without any deformation or plasma treatment.
Figure 3B:
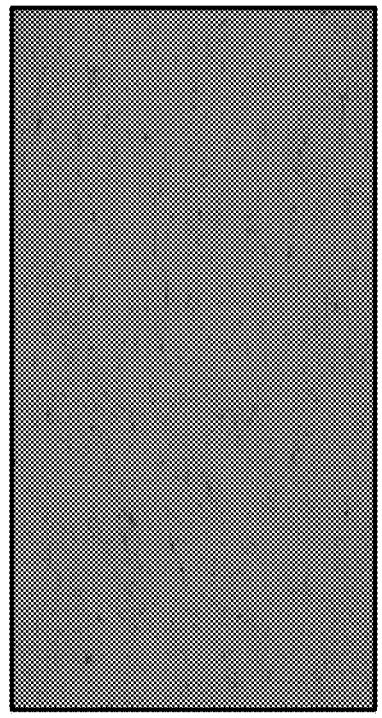
Figure 3C:
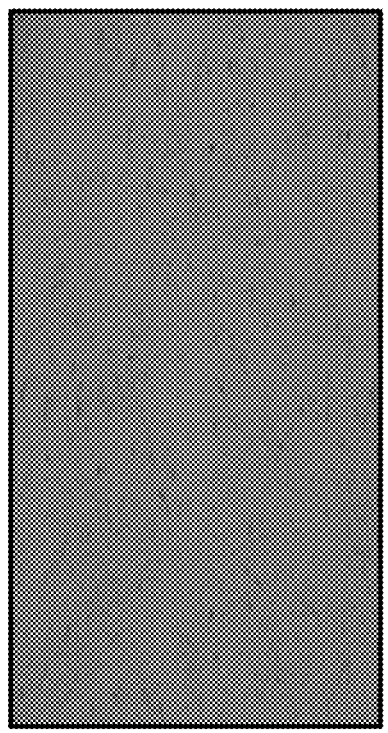
Figure 3D:
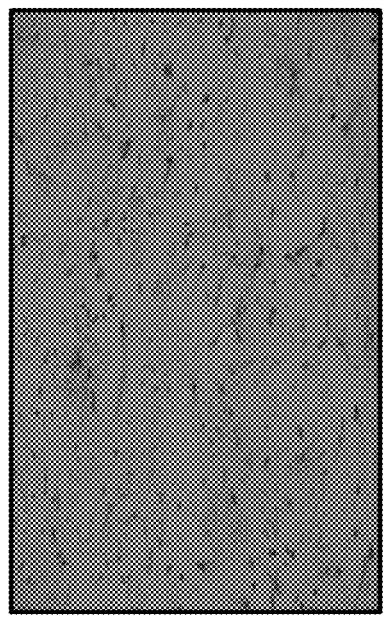
FIG. 3D is a photomicrograph showing a surface that has been plasma and poly-L-Lysine treated.
Figure 3E:
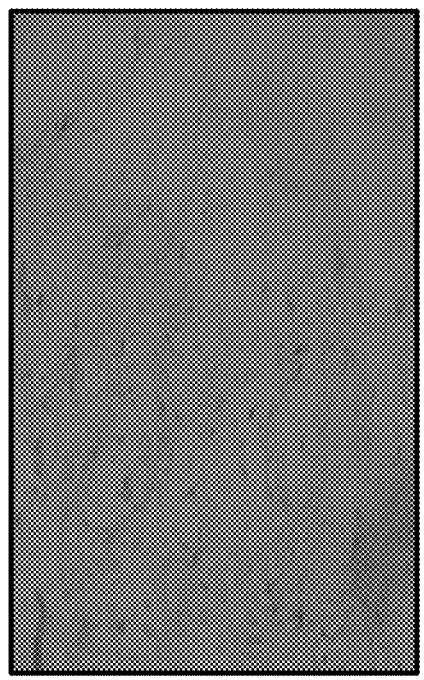
FIG. 3E is a photomicrograph showing a side of the airfoil shape that has been deformed and plasma and Poly-L-Lysine treated, demonstrating cell adhesion post modification.

Post modification, plasma treatment (Thierry, Femto Plasma System V1) of the deformed petri-dishes for 25 seconds in a cleanroom, immediately followed by placement of Poly-L-Lysine (Sigma-Aldrich P4832) for 5 minutes ensured proper cell adhesion for pulsating flow experiments. FIGS. 3A-3C show primary rat cardiac progenitor cells on three separate cell culture dishes without any deformation or plasma treatment. FIG. 3D shows a surface that has been plasma and poly-L-Lysine treated. FIG. 3E shows a side of the airfoil shape that has been deformed and plasma and Poly-L-Lysine treated, demonstrating cell adhesion post modification.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, singular forms like "a," or "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The term and/or is used herein to mean both "and" as well as "or". For example, "A and/or B" is construed to mean A, B or A and B.

The transition term "comprising" is inclusive of the transition terms "consisting essentially of" and "consisting of" and can be interchanged for "comprising".

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A tissue harvester comprising: a substrate having an airfoil shape; and a textured surface disposed upon the substrate, where the textured surface comprises a plurality of patterns; where the tissue harvester is disposed in a flow field along with cells that are to be generated on the tissue harvester; and where the textured surface is formed by a block copolymer that has one of its domains etched, leaving behind the other domain in the form of pillars to texture the surface.

2. The tissue harvester of claim 1, where the substrate and the textured surface are monolithic.

3. The tissue harvester of claim 1, where the textured surface is bonded to the substrate.

4. The tissue harvester of claim 1, where the substrate and/or the textured surface comprise a polymer, a ceramic or a metal.

5. The tissue harvester of claim 1, where the block copolymer is poly(styrene-b-vinyl pyridine), poly(styrene-b-butadiene), poly(styrene-b-isoprene), poly(styrene-b-methyl methacrylate), poly(styrene-b-alkenyl aromatics), poly(isoprene-b-ethylene oxide), poly(styrene-b-(ethylene-propylene)), poly(ethylene oxide-b-caprolactone), poly(butadiene-b-ethylene oxide), poly(styrene-b-t-butyl (meth) acrylate), poly(methyl methacrylate-b-t-butyl methacrylate), poly(ethylene oxide-b-propylene oxide), poly(styrene-b-tetrahydrofuran), poly(styrene-b-isoprene-b-ethylene oxide), poly(styrene-b-dimethylsiloxane), poly(methyl methacrylate-b-dimethylsiloxane), or a combination comprising at least one of the foregoing block copolymers.

6. The tissue harvester of claim 1, where the pillars have a diameter of less than 100 nanometers.

7. The tissue harvester of claim 1, where the pillars have a diameter of less than 100 micrometers.

8. The tissue harvester of claim 1, where the textured surface comprises objects having square, rectangular, ellipsoidal, triangular, circular, or polygonal cross-sections.

9. A method comprising: disposing upon a substrate a textured surface; where the substrate has an airfoil shape and where the textured surface where the textured surface comprises nanometer or micrometer sized pillars; contacting the tissue harvester with biological cells whose proliferation under different conditions is desired; and disposing the tissue harvester in a flow field such that cells disposed on the tissue harvester at different locations may experience different flow fields; where the flow field is a pulsating flow field.

10. The method of claim 9, where the cells adhere to the tissue harvester.

11. The method of claim 10, where the cells proliferate on the tissue harvester.

12. The method of claim 11, further comprising removing the proliferated cells from the tissue harvester.

13. The method of claim 9, where the cells experience a gradient in flow fields from laminar to turbulent.

14. A tissue harvester comprising: a substrate having an airfoil shape; and a textured surface disposed upon the substrate, where the textured surface comprises a plurality of patterns; where the tissue harvester is disposed in a flow field along with cells that are to be generated on the tissue harvester; and where the patterns are projected into the surface of the substrate.

* * * * *